United States Patent [19]

Warawa et al.

[11] Patent Number: 4,879,288
[45] Date of Patent: Nov. 7, 1989

[54] NOVEL DIBENZOTHIAZEPINE ANTIPSYCHOTIC

[75] Inventors: Edward J. Warawa, Wilmington, Del.; Bernard M. Migler, Cherry Hill, N.J.

[73] Assignee: ICI Americas Inc., Wilmington, Del.

[21] Appl. No.: 28,473

[22] Filed: Mar. 20, 1987

[30] Foreign Application Priority Data

Mar. 27, 1986 [GB] United Kingdom ............... 8607684

[51] Int. Cl.$^4$ ................. C07D 417/04; A61K 31/555
[52] U.S. Cl. ..................................... 514/211; 540/551
[58] Field of Search ......................... 540/551; 514/211

[56] References Cited

U.S. PATENT DOCUMENTS

| | | | |
|---|---|---|---|
| 3,325,497 | 6/1967 | Fouche | 544/381 |
| 3,389,139 | 6/1968 | Schmutz et al. | 544/381 |
| 3,459,745 | 8/1969 | Fouche | 540/575 |
| 3,539,573 | 11/1970 | Schmutz et al. | 544/381 |
| 3,723,466 | 3/1973 | Malon | 540/551 |
| 3,755,340 | 8/1973 | Hoehn et al. | 424/267 |
| 3,761,481 | 9/1973 | Nakanishi | 540/551 |
| 3,928,356 | 12/1975 | Umio et al. | 424/250 |
| 3,962,248 | 6/1976 | Schneider | 540/551 |
| 4,096,261 | 6/1978 | Horrom et al. | 424/250 |
| 4,097,597 | 6/1978 | Horrom et al. | 424/250 |
| 4,308,207 | 12/1981 | Hunziker et al. | 424/250 |

FOREIGN PATENT DOCUMENTS

721822 4/1969 Belgium .
1620188 4/1970 Fed. Rep. of Germany .

OTHER PUBLICATIONS

Chemical Abstracts, vol. 93, No. 11, 15th Sep. 1980, p. 727, col. 1, abstract No. 114451y, Columbus, OH, US; abstract of: "Piperazinyldibenzazepine", RES. DISCL. 1980, 192, 158–159.

"Piperazinyldibenzazepine", RES. DISCL. 1980, 192, 158–159.

Tobler, E. and Foster, D. J. *Helv. Chim. Acta.*, 48:336 (1965).

Ther, L. and Schramm, H. *Arch. Int. Pharmacodyn.*, 138:302 (1962).

Puech, A. J., Simon, P. and Boissier, J., *Eur. J. Pharm.*, 50:291 (1978).

Swerdlow, U. R. and Koob, G. F., *Pharmacol. Biochem. and Behav.*, 23:303 (1985).

Carlson, A. and Lindquist, M., *Acta. Pharmac. Tox.*, (1963) 20:140.

Saller, L. F. and Salama, A. I., *J. Chromatography*, (1984) 309:287.

Herz, A., *Int. Rev. Neurobiol.*, (1960) 2:229–277.

Barany, S., Haggstrom, J. H. and Gunne, L. M., *Acta. Pharmacol. et. Toxicol.*, (1983) 52:86.

Liebman, J. and Neale, R., *Psychopharmacology* (1980), 68:25–29.

Weiss, B. and Santelli, S., *Science*, (1978), 200:799–801.

Gunne, A. and Barany, S., *Psychopharmacology*, (1979), 63:195–198.

*Primary Examiner*—Mark L. Berch
*Attorney, Agent, or Firm*—Rosemary M. Miano; Thomas E. Jackson; James T. Jones

[57] ABSTRACT

11-[4-[2-(2-Hydroxyethoxy)ethyl]-1-piperazinyl]dibenzo[b,f][1,4]thiazepine is disclosed as a neuroleptic with a much reduced incidence of side effects such as acute dystonia and dyskinesia and tardive diskinesia.

8 Claims, No Drawings

NOVEL DIBENZOTHIAZEPINE ANTIPSYCHOTIC

SUMMARY AND BACKGROUND OF THE INVENTION

This invention concerns a novel dibenzothiazepine compound useful for its antidopaminergic activity, for example, as an antipsychotic or neuroleptic.

Previous attempts at finding compounds useful in a variety of applications have included U.S. Pat. No. 3,539,573 to Schmutz et al. which discloses selected dibenzothiazepines and dibenzodiazepines as being useful for a variety of medical conditions including as neuroleptic-antidepressants, or neuroleptics. U.S. Pat. No. 3,389,139 to Schmutz et al. teaches compounds based on 6-basic substituted morphanthridines as neuroplegics, neuroleptics and analgesics, with selected compounds being useful for treating psychotic conditions. U.S. Pat. No. 4,097,597 to Horrom et al. discloses dibenzodiazepine derivatives useful as antischizophrenics.

A compound of the following formula I

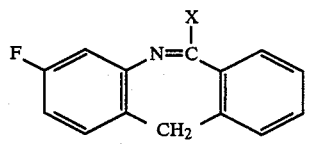

in which X may be as shown in formula Ia

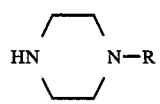

and R may be (CH$_2$CH$_2$O )$_2$H, has been Anonymously disclosed in *Res. Discl.* (1980), 192: 158-9.

Compounds used as antipsychotics and neuroleptics have, however, been plagued by the problems of undesired side effects. Such side effects include acute dyskinesias, acute dystonias, motor restlessness, pseudo-Parkinsonism and tardive dyskinesias (TD). Acute syndromes usually have an early onset, for example, 1 to 5 days for acute dystonias and dyskinesias, and may include torsion spasms, muscle spasms and dystonia of the face, neck or back with protrusion of the tongue and tonic spasms of the limbs (dyskinesia). Tardive dyskinesia has a time of maximal risk after months or years of treatment. TD's comprise oral-facial dyskinesia, lingual-facial-buc-cal-cervical dystonias sometimes with involvement of the trunk and extremities. TD's also include repetitive stereotypical movements of the face, tongue and limb such as sucking and smacking of the lips, lateral jaw movements and protrusions of the tongue. When the antipsychotic drug treatment is stopped the symptoms continue, often for months or years. These involuntary movements constitute the most undesirable side effect of antipsychotic drug treatment; for example, the percentage of patients that develop TD has been variously reported to be as high as 20 percent. Thus, there still remains a need for compounds which exhibit antidopaminergic activity without the side effects heretofore experienced with previous compounds.

DESCRIPTION OF THE INVENTION

This invention is a compound of formula II:

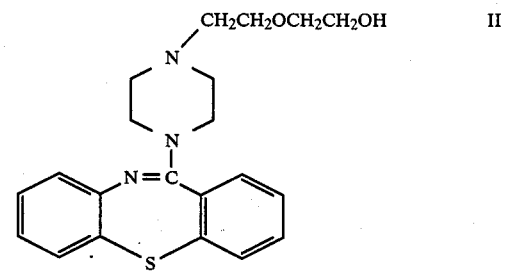

and salts thereof, for example and especially pharmaceutically acceptable salts. Such a compound is useful because of its antidopaminergic activity, for example, as an antipsychotic agent or as a treatment for hyperactivity. Such a compound is of even greater interest in that it may be used as an antipsychotic agent with a substantial reduction in the potential to cause side effects such as acute dystonia, acute dyskinesia, pseudo-Parkinsonism as well as tardive dyskinesia which may result from the use of other antipsychotics or neuroleptics.

The compound of formula II may be made by a variety of methods including taking the lactam of formula III:

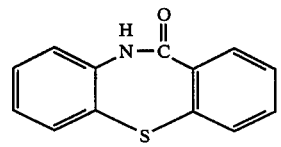

which may be prepared by methods well known in the literature, for example, as described by J. Schmutz et al. *Helv. Chim. Acta.*, 48:336 (1965), and treating the lactam of formula III with phosphorous oxychloride (POCl$_3$) to generate the imino chloride of formula IV:

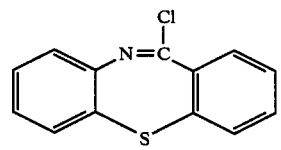

The imino chloride of formula IV may also be generated with other agents such as thionyl chloride or phosphorous pentachloride. The imino chloride is then reacted with 1-hydroxyethoxyethylpiperazine of formula V:

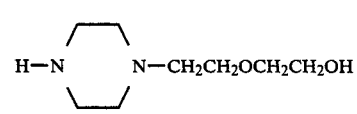

to give the compound of formula II.

Alternatively, one may convert the lactam of formula III into a thiolactam of formula VI:

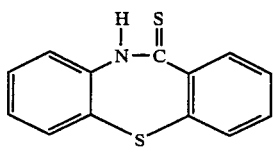

VI by, for example, reacting the lactam of formula III with a polysulfur compound such as phosphorous pentasulfide or 2,4-bis(4-methoxyphenyl)-1,3-dithia-2,4-diphosphetane-2,4-disulfide (Lawesson's Reagent, obtained from Aldrich).

The lactam of formula VI may then be converted into a thioether of formula VII:

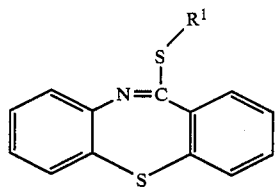

VII where $R^1$ is chosen such that $S-R^1$ is a leaving group, for example, $R^1$ may be (1-3C)alkyl, for example, methyl, by alkylation with an alkyl iodide, for example, methyl iodide. The piperazine of formula V is then reacted with the thioether of formula VII to give the compound of formula II.

A preferred way of making the compound of formula II is as follows. A compound of formula XII:

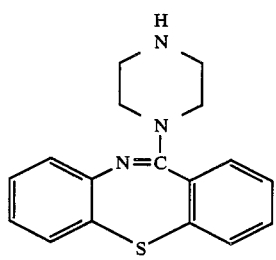

XII is reacted with a compound of formula XIII:

$ZCH_2CH_2OCH_2CH_2OH$     XIII (in which Z is an atom or group removable as an anion) and, whereafter, when the compound of formula II is obtained as a base and a salt is required, reacting said compound of formula II obtained in the form of a base with an acid to afford a salt and when the compound of formula II is obtained as a salt and a base is required, neutralizing said compound of formula II obtained in the form of a salt to afford the said base.

A compound of formula XIII is advantageously used in which Z represents a mesyloxy or tosyloxy group, but Z is preferably halogen. Z most preferably represents a chlorine atom.

The reaction is conveniently carried out in the presence of a solvent, preferably a polar organic solvent, more preferably an alcohol, especially a (1-6C)alkanol, for example, methanol, ethanol, propanol, butanol, pentanol, hexanol and isomers thereof especially n-propanol. Other convenient solvents include aprotic solvents such as for example dimethylforamide or N-methyl pyrrolidone. If desired, an appropriate mixture of polar organic and aprotic solvents may be used.

If desired the compound of formula XII may be employed in the form of a salt, but where such a salt is used it is neutralized to afford the corresponding free base prior to reaction with the compound of formula XIII, for example, by in situ neutralization. Such neutralization is advantageously conducted in the presence of a basic substance, preferably an alkali metal carbonate or an alkaline earth metal carbonate, more preferably sodium or potassium carbonate.

Additionally an alkali metal halide, advantageously in a catalytic amount, may optionally be added to the reaction mixture. Sodium iodide is a preferred alkali metal halide. The effect of this addition is to convert Z in formula XIII to a halogen, preferably iodine, whereby the reaction of the compound of formula XII with the compound of formula XIII may be promoted.

The reaction is conveniently performed at ambient temperature or at an elevated temperature, preferably at a temperature between ambient and the reflux temperature of the reaction mixture, more preferably at the reflux temperature, and advantageously the reaction is carried out for an extended period of time, preferably 15 to 30 hours, more preferably about 24 hours.

The salts of the compound of formula II prepared according to the process of the present invention are preferably the pharmaceutically acceptable salts, but other salts may also be prepared. Such other salts may, for example, find use in the preparation of the compound of formula II and the pharmaceutically acceptable salts thereof. Convenient salts may be selected from those pharmaceutically acceptable salts known in the art. These may be obtained, for example, by reacting the compound of formula II with a convenient acid, such as for example, hydrochloric acid, maleic acid, fumaric acid, citric acid, phosphoric acid, methane sulfonic acid, and sulfuric acid. A preferred salt is the hemi-fumarate salt.

The compound of formula XII is preferably prepared by the reaction of an 11-substituted-dibenzo[b,f][1,4]-thiazepine of the formula XIV:

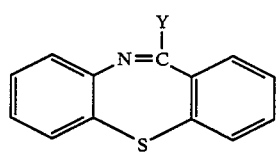

XIV in which the substituent Y represents an atom (or a group) removable as an anion, with piperazine. A compound of formula XIV may, for example, be used in which Y represents an alkoxy, alkylthio or sulfonate group. Thus, Y may, for example, represent (1-6C)-alkoxy, preferably methoxy or ethoxy, or (1-6C)-alkylthio, preferably methylthio or ethylthio, or Y may represent a tosyloxy group. Preferably Y represents a halogen atom, for example bromine but especially chlorine. The reaction is conveniently performed at ambient temperature or at an elevated temperature, preferably at a temperature between ambient and the reflux temperature of the reaction mixture, more preferably at the reflux temperature, and advantageously the reaction is carried out in the presence of an inert organic solvent, preferably an aromatic hydrocarbon solvent, such as, for example, xylene or toluene. The reaction is conveniently performed for 2 to 15 hours, preferably 3 to 10 hours, more preferably about 5 hours.

The compounds of formula XIV may, for example, be prepared by methods analogous to those known in the art or, where Y represents halogen, preferably by reacting dibenzo[b,f][1,4]-thiazepine11(10-H)one of formula XV:

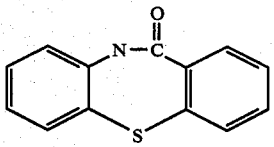   XV with a halogenating agent, preferably a phosphorous pentahalide or oxyhalide (POHal₃). The above halide is selected, for example, from chlorine or bromine, especially chlorine. Where it is desired to prepare a compound of formula XIV in which Y represents a chlorine atom, a preferred halogenating agent is phosphorous oxychloride (POCl3) Where it is desired to prepare a compound of formula XIV in which Y represents a bromine atom, a preferred halogenating agent is phosphorous pentabromide. The reaction may advantageously be carried out in the presence of an N,N-disubstituted aniline, preferably N,N-di[1-6C]alkyl) substituted aniline, more preferably an N,N-dimethylaniline. The reaction is advantageously effected at an elevated temperature, preferably at the reflux temperature of the reaction mixture, conveniently for between 3 to 15 hours, preferably 4 to 10 hours, more preferably 6 hours.

The compound of formula XV may, for example, be prepared according to methods known in the art, for example, by the method disclosed by J. Schmutz et al. *Helv. Chim Acta,* 48: 336 (1965). Preferably the compound of formula XV is prepared by cyclizing a compound selected from compounds of the formulae XVI, XVII, XVIII

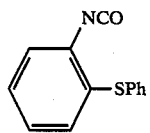   XVI

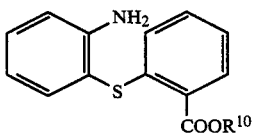   XVII

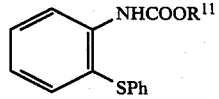   XVIII and wherein Ph is phenyl and OR$^{10}$ and OR$^{11}$ represent an atom or group removable as an anion whereby to form a compound of formula XV. The cyclization is advantageously effected under acidic conditions, preferably in the presence of an acid of sulfur or phosphorous, for example, concentrated sulfuric acid or more preferably polyphosphoric acid. The reaction is advantageously carried out at an elevated temperature, preferably at a temperature of from 60 ° 120°C., especially from 95 ° 105°C., advantageously for about 4–8 hours, preferably about 6 hours.

In the compounds of formulae XVII and XVIII R$^{10}$ and R$^{11}$ may, for example, represent hydrogen, (1-6-C)alkyl or optionally substituted phenyl. Preferably R$^{10}$ represents methyl or ethyl and R$^{11}$ preferably represents methyl, ethyl or phenyl, but most preferably phenyl.

The compound of formula XVII may, for example, be obtained by the reaction of 2-amino diphenysulfide and phenyl chloroformate.

The new compound of this invention is a central nervous system depressant and may be used as a tranquilizer for the relief of hyperactivity states, for example, in mice, cats, rats, dogs and other mammalian species, and additionally for the management of psychotic states in man, in the same manner as chlorpromazine. For this purpose a compound of formula II, or non-toxic physiologically acceptable acid addition salts thereof, may be administered orally or parenterally in a conventional dosage form such as tablet, pill, capsule, injectable or the like. The dosage in mg/kg of body weight of a compound of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula II will be at least about 1.0 mg/kg of body weight per day for mammals with a maximum dosage for a small mammal such as a dog, of about 200 mg/kg per day. For humans, a dosage of about 1.0 ° 40 mg/kg per day will be effective, for example, about 50 to 2000 mg/day for an average person weighing 50 kg. The dosage can be given once daily or in divided doses, for example, 2 to 4 doses daily, and such will depend on the duration and maximum level of activity of a particular compound. The dose may be conventionally formulated in an oral or parenteral dosage form by compounding about 25 to 500 mg per unit of dosage of conventional vehicle, excipient, binder, preservative, stabilizer, flavor or the like as called for by accepted pharmaceutical practice, for example, as described in U.S. Pat. No. 3,755,340. The compound of this invention may contained in or co-administered with one or more known drugs.

No overt toxicity has been observed for this compound at therapeutic doses.

EXAMPLE 1

11-[4-[2-(2-Hydroxyethoxy)ethyl]-1-piperaziny]dibenzo[b,f][1,4]thiazepine (Formula II)

A 2 liter round-bottom flask equipped with a magnetic stirring bar and reflux condenser with a nitrogen inlet was charged with 115.0 grams (g) (0.506 mole) of dibenzo[b,f][1,4]thiazepine-11(10-H)-one (made by the method disclosed by J. Schmutz et al. *Helv. Chim. Acta.,* 48: 336 (1965)), phosphorous oxychloride 700 ml (7.5 moles) and N,N-dimethylaniline 38.0 g (0.313 mole). The grey suspension was heated to gentle refluxing using a heating mantle. After 6 hours of heating, the resulting amber solution was allowed to cool to room temperature (from about 18°-25°C.) and was analyzed by thin-layer chromatography (TLC) using silica gel plates, developed with ether-hexane (1:1) and detected with ultraviolet light. Analysis revealed the desired imino chloride, R$_f$=0.70, and an absence of starting lactam.

Excess phosphorous oxychloride, was removed in vacuo using a rotary evaporator. The brown syrupy residue was dissolved in 1500 milliliters (ml) of toluene, treated with 500 ml of an ice-water mixture and stirred for 30 minutes. The toluene layer was separated, washed twice with 200 ml of water and dried with anhydrous magnesium sulfate. After removal of the drying agent by filtration, the filtrate was concentrated in vacuo using a rotary evaporator to give the crude imino chloride as a light yellow solid: 115.15 g (92.6% yield): melting point (mp) 106°–108°.

The above imino chloride, 114.0 g (0.464 mole), and 1000 ml of xylene were placed in a 3 liter 3-necked round bottom flask equipped with a mechanical stirrer, reflux condenser with a nitrogen inlet and a heating mantle. The resulting yellow solution was treated with 161.7 g (0.928 mole) of 1-(2-hydroxyethoxy)ethylpiperazine, rinsing with 200 ml of xylene. This reaction mixture was heated at gentle reflux for 30 hours during which time a brown oil began to separate. The reaction mixture was cooled to room temperature. Thin layer chromatography (TLC) analysis (silica gel, methanol: methylene chloride (1:9), ultraviolet light and iodine detection) indicated complete consumption of the imino chloride and the presence of the desired product with $R_f=0.5$ (approximately). The mixture was treated with 700 ml of 1 Normal (1N) sodium hydroxide and 700 ml of diethyl ether. The layers were separated and the aqueous phase was extracted once with 500 ml of diethyl ether. The combined ether extract was treated with 400 ml of 1N hydrochloric acid. The acidic extract was treated with solid sodium carbonate portionwise to give a brown oil which was extracted four times with 400 ml of methylene chloride. These methylene chloride extracts were combined and dried with anhydrous magnesium sulfate. The drying agent was removed by filtration and the filtrate was concentrated in vacuo using a rotary evaporator to yield the crude product as a viscous amber oil, 194.5 g, which was purified by flash chromatography as follows The crude product in a minimum of methylene chloride was applied to a 3.5 inch×20 inch column of silica gel packed in methylene chloride. The column was eluted under nitrogen pressure with 4 liter portions each of methylene chloride, and 2%, 4% and 6% methanol:methylene chloride (2:98: 4:96, 6:94 respectively) while 250 ml fractions were collected. These fractions were monitored by TLC (conditions cited below). The title product began to elute with 4% methanol:methylene chloride (4:96). Combination of the pure fractions and removal of the solvent in vacuo gave the title product 138.7 g (77.7% yield). TLC using silica gel, methanol:methylene chloride (1:9) with ultraviolet (u.v.) and iodine detection showed a single compound; $R_f=0.5$.

Analysis calculated for: $C_{21}H_{25}N_3O_2S$: C, 65.77; H, 6.57; N, 10.75. Found: C, 65.25; H, 6.52; N, 10.62.

EXAMPLE 2

11-[4-[2-(2-Hydroxyethoxy)ethyl]-1-piperazinyl]dibenzo[b,f][1,4]thiazepine, hydrochloride salt A portion of a product made by the method of Example 1, 10.0 g (26 millimoles (mmol)), was dissolved in 40 ml of ethanol, treated with 30 ml of a saturated ethanolic hydrogen chloride solution and stirred until a turbidity ensued (about 20 minutes). The heterogeneous solution was then added to 500 ml of diethyl ether with stirring. The resulting white crystalline salt was collected by filtration, washed with diethyl ether and dried in vacuo in a drying pistol over refluxing ethanol to give the title compound, 10.7 g, m.p. 218°–219°.

Analysis calculated for: $C_{21}H_{25}N_3O_2S.2HCl$: C, 55.26; H, 5.96; N, 9.20. Found: C, 55.17; H, 6.00; N, 9.07.

EXAMPLE 3

11-[4-[2-(2-Hydroxyethoxy)ethyl]-1-piperazinyl]dibenzo[b,f][1,4]thiazepine, maleate A portion of a product made by the method of Example 1, 3.6 g (9.38 mmol), was dissolved in 25 ml of ethanol and treated with 1.08 g (9.38 mmol) of maleic acid. This mixture was heated with stirring until solution was complete and left to cool to room temperature. Addition of diethyl ether resulted in a precipitate which was collected by filtration, washed with diethyl ether and dried in vacuo in a drying pistol over refluxing ethanol to give the title compound, 4.2 g, m.p. 129°–130°.

Analysis calculated for: $C_{21}H_{25}N_3O_2S.C_4H_4O_4$: C, 60.10; H, 5.85; N, 8.41. Found: C, 60.08: H, 5.85; N, 8.36.

EXAMPLE 4

11-[4-[2-(2-Hydroxyethoxy)ethyl]-1-piperazinyl]dibenzo[b,f][1,4]thiazepine, hemifumarate A portion of a product made by the method of Example 1, 2.1 g (5.47 mmol) was dissolved in 20 ml of ethanol and treated with 0.67 g (5.7 mmol) of fumaric acid. Upon heating, complete solution was effected for a few minutes after which the salt began to crystallize. After one hour at room temperature, the resulting solid was collected by filtration and dried in vacuo in a drying pistol over refluxing ethanol to give the title compound, 2.4 g, m.p. 172°–173°.

Analysis calculated for: $C_{21}H_{25}N_3O_2S.0.5C_4H_4O_4$: C, 62.57; H, 6.16; N, 9.51. Found: C, 62.15; H, 6.19; N, 9.25.

EXAMPLES 5–8

A number of tests are recognized as showing antidopaminergic activity of a compound and/or as being predictive of antipsychotic activity in mammals. For these tests a compound of formula II in the form of a salt (for example, as described in Example 2) was used. All dosages in the tables are expressed as free base.

EXAMPLE 5

Apomorphine-Induced Climbing in Mice

This test has been described by Ther and Schramm [*Arch int. Pharmacodyn.*, 138: 302 (1962); Peuch, Simon and Boissier, *Eur. J. Pharm.*, 50: 291 (1978)]. Mice that are administered an appropriate dose of apomorphine (a dopamine agonist) will climb the walls of a cage or other suitable structure and remain at or near the top for 20–30 minutes. Untreated mice on the other hand will occasionally climb up and then climb down. The exaggerated climbing of apomorphine-treated mice can be antagonized by pretreatment with dopamine blocking agents. The antagonism of apomorphine-induced climbing in mice is therefore an indication of the potential dopamine blocking activity of the agent. Since dopamine blocking agents are typically antipsychotic agents, the test is considered to be evidence for potential antipsychotic activity of the agent. The vehicle itself [hydroxypropylmethylcellulose (HPMC) 0.5% w/v, polyoxyethylene (20) sorbitan monooleate (Tween 80) .1% w/v, and distilled water] or the vehicle with the test compound of the present invention was administered orally to twenty mice in graded doses. After 30 minutes, apomorphine HCl was administered subcutaneously at 1.25 mg/kg and the mice were placed in cages containing 28 horizontal rungs, upon which the mice could climb. Thirteen minutes later they were scored for climbing. The climbing score was the mean of the highest and lowest rungs on which the mouse climbed during a one-minute time period from 13 ° 14 minutes after apomorphine. The results in 24-hour fasted mice are presented in Table 1. The compound of the present invention antagonized the climbing, a result predictive of antipsychotic activity.

TABLE 1

| Compound Tested | Dosages (mg/kg i.p.) | Mean Climb Score |
| --- | --- | --- |
| Vehicle | — | 24 |
| Formula II (HCl salt) | 10 | 24 |
| Formula II (HCl salt) | 20 | 15 |
| Formula II (HCl salt) | 40 | 2 |
| Formula II (HCl salt) | 80 | 0 |

EXAMPLE 6

Antagonism of Apomorphine-Induced Hyperactive in Rats

This test has been described by Swerdlow and Koob [*Pharmacol. Biochem. and Behav.*, 23: 303 (1985)]. Rats that are administered amphetamine at a moderate dose become hyperactivity. The hyperactivity can last for several hours, and can be measured in various ways, for example, by counting the number of times the rat walks from one end of a long alley to the other end. The physiological basis for amphetamine-induced hyperactivity is thought to be the release of excessive amounts of dopamine in the brain. The hyperactivity of anphetamine-treated rats can be antagonized (prevented) by pretreatment with dopamine-blocking agents. The antagonism of amphetamine-induced hyperactivity in rats is, therefore, an indication of the potential dopamine-blocking and potential antipsychotic activity of the agent. The compound of the present invention as the HCl salt or the vehicle (vehicle is defined in Example 5) were administered orally to 20 rats and aaphetamine was then injected intraperitoneally. Activity (walking back and forth in a long alley) was recorded for two hours. The activity scores are presented in Table 2. The compound of the present invention antagonized the hyperactivity, a result predictive of antipsychotic activity.

TABLE 2

Antagonism of Amphetamine-Induced Hyperactivity in Rats

| Compound Tested | Dosages (mg/kg p.o.) | Activity Score (0-2 Hr) (Mean Number of Crossings of Center Line of Alley) | |
| --- | --- | --- | --- |
| Vehicle | | 148 | |
| Formula II (HCl salt) | 10 | 118.3 | $p < .05$ |
| Formula II (HCl salt) | 20 | 92.4 | $p < .0005$ |
| Formula II (HCl salt) | 40 | 64.3 | $p < .0005$ |
| Formula II (HCl salt) | 80 | 39.8 | $p < .0005$ |

EXAMPLE 7

Effect of Test Compound on Rat Striatal Levels of Dihydroxyphenylacetic Acid (DOPAC) and Homovanillic Acid (HVA)

Among the various pharmacological effects of antipsychotics, their action as dopamine antagonists in the brain has been extensively investigated. Enhancement of dopamine metabolism (dihydroxyphenylacetic acid and homovanillic acid (DOPAC and HVA)) by antipsychotic agents has been attributed to a blockade of dopamine receptors [A. Carlson and M. Lindquist, *Acta. Pharmac. Tox.*, (1963) 20: 140]. The effects of a compound of the invention on DOPAC and HVA levels in the rat striatum were measured by HPLC using electrochemcial detection according to the method of Saller and Salama [*J. Chromatography*, (1984) 309: 287]. A compound of Formula II (HCl salt) was suspended in the vehicle (as defined in Example 5) and administered intraperitoneally (i.p.) to eight Sprague Dawley rats with the following results.

| Compound Tested | Dosages (mg/kg i.p.) | % Control DOPAC | HVA |
| --- | --- | --- | --- |
| Formula II (HCl salt) | 10 | 145 | 140 |
| Formula II (HCl salt) | 20 | 220 | 210 |
| Formula II (HCl salt) | 40 | 300 | 260 |

EXAMPLE 8

Conditioned Avoidance in Squirrel Monkeys

The conditioned avoidance test has been described by Herz, A., *Int. Rev. Neurobiol.*, (1960) 2: 229-277. In this test, a warning stimulus is presented for five seconds. The monkeys are trained to press a lever to turn off the warning stimulus thereby avoiding the delivery of electric shocks at 1/sec for 10 seconds that would begin at the end of the warning stimulus. If there is no response during the warning stimulus (no avoidance response) and the shocks begin, a response during the shocks stops the shocks. Trials of this type are repeated every minute for six hours. Antipsychotic drugs produce a marked reduction in responding to the warning stiulus. A compound of the present invention Formula II (HCl salt) was administered orally and the conditioned avoidance test was administered. The vehicle used was that defined in Example 5. The results are presented in Table 3. The compound of the present invention produced a marked reduction of avoidance responses, a result predictive of antipsychotic activity.

TABLE 3

| Conditioned Avoidance in Squirrel Monkeys | | |
| --- | --- | --- |
| Compound Tested | Dosages (mg/kg p.o.) | Number of Monkeys Scoring 75% (Or Less) Avoidance Responses/Number Tested |
| Vehicle | — | 0/20 |
| Formula II (HCl salt) | 5 | 0/4 |
| Formula II (HCl salt) | 10 | 15/20 |
| Formula II (HCl salt) | 20 | 19/20 |

EXAMPLE 9

Test for Production of Acute Dystonia, Acute Dyskinesia, and Tardive Dyskinesia One test for predicting whether or not a potential antipsychotic drug will produce involuntary movements of the type described in this application, such as acute dystonia and acute dyskinesia, is in the haloperidol-sensitized and drug-naive cebus monkey. Such tests are described by Barany, Haggstrom and Gunne, *Acta Pharmacol. et Toxicol.*, (1983) 52:86; J. Liebman and R. Neale, *Psychopharmacology*, (1980), 68:25-29; and B. Weiss and S. Santelli, *Science*, (1978), 200:799-801. (Also see a discussion of test results in A. Gunne and S. Barany *Psychopharmacology*, (1979), 63:195-198). Also, antipsychotic drugs that are known to produce tardive dyskinesia in schizophrenic patients produce acute dyskinetic and dystonic reactions in the haloperidol-sensitized cebus monkey. Clozapine, the only antipsychotic drug for which there has been no tardive dyskinesia reported, does not produce a dyskinetic reaction in sensitized cebus monkeys. The compound of Formula II, clozapine, thioridazine or haloperidol were each orally administered to sensitized cebus monkeys. They were then observed in their home cages continuously for eight hours and occurrences of dyskinetic reactions noted. The results are presented in Table 4. The compound of the present invention exhibited markedly fewer dyskinetic and dystonic reactions as compared to the known dyskinetic drugs haloperidol or thioridazine. In addition to producing fewer reactions, the intensity of the reactions produced by the compound of the present invention was less than that of thioridazine or haloperidol. For example, at 20 mg/kg p.o. the compound of the present invention produced reactions in two of thirteen monkeys; however, one of these reactions was extremely weak, lasting only about five minutes. The reaction at 10 mg/kg was also weak, lasting only about twenty seconds. By contrast, the reactions produced by thioridazine or haloperidol typically lasted several hours and were of moderate or high intensity.

TABLE 4
Dyskinetic Reactions in Sensitized Cebus Monkeys

| Compound Tested | Dosages (mg/kg p.o.) | Number of Monkeys with Dyskinetic Reactions/Number Tested |
| --- | --- | --- |
| Haloperidol | 1.0 | 13/13 |
| Thioridazine | 10 | 11/13 |
| Clozapine | 10 | 0/1 |
| Clozapine | 20 | 0/13 |
| Clozapine | 40 | 0/11 |
| Clozapine | 60 | 0/5 |
| Formula II (HCl salt) | 2.5 | 0/13 |
| Formula II (HCl salt) | 5 | 1/13 |
| Formula II (HCl salt) | 10 | 1/13 |
| Formula II (HCl salt) | 20 | 2/13 |
| Formula II (HCl salt) | 40 | 0/4 |

EXAMPLE 10

(a) 11-[4-[2-(2-Hydroxyethoxy)ethyl]-1-piperazinyl]-dibenzo[b,f][1,4]thiazepine. (Formula II)

11-Piperazinyldibenzo[b,f][1,4]thiazepine dihydrochloride (25 mmole), sodium carbonate (150 mmole), sodium iodide (1 mmole) and 2-chloroethoxyethanol (27 mmoles) were combined together in n-propanol (60 ml) and N-methyl pyrrolidone (15 ml). The reaction was heated at reflux for 24 hours. Ethyl acetate (75 ml) was added and the reaction washed with water (2×250 ml). The organic phase was dried over magnesium sulfate and the solvent removed in vacuo to give an oil. The oil was dissolved in ethanol and treated with fumaric acid (4 mmole). The product was isolated as the hemi-fumarate salt in 78% yield, melting point (m.p.) 172°-173°.

The thiazepine derivative used as a starting material was prepared as follows:

(b) 11-Piperazinyl-dibenzo[b,f][1,4]thiazepine.

Piperazine (1.7 mole) was dissolved in warm toluene (about 50°C.) (750 ml) and 11-chloro-dibenzo[b,f][1,4]-thiazepine was added. The reaction was heated to reflux and maintained at this temperature for 5 hours. After cooling to ambient temperature the reaction was filtered to remove piperazine hydrochloride, and the organic phase was washed several times with water to remove excess piperazine. The organic phase was dried over magnesium sulfate and after filtration the solvent was removed in vacuo to give the product as an oil. The oil was dissolved in ethanol and treated with a solution of hydrogen chloride in ethanol.

11-Piperazinyl-dibenzo[b,f][1,4]thiazepine was isolated as the dihydrochloride salt in about 88% yield.

(c) 11-Chloro-dibenzo[b,f][1,4]thiazepine

A 2 liter round-bottom flask equipped with a magnetic stirring bar and reflux condenser with a nitrogen inlet was charged with 115.0 g (0.506 mole) of dibenzo[b,f][1,4]thiazepine-11(10-H)one, phosphorous oxychloride 700 ml (7.5 moles) and N,N-dimethylaniline 38.0 g (0.313 mole). The grey suspension was heated to gentle refluxing using a heating mantle. After 6 hours of heating, the resulting amber solution was allowed to cool to room temperature (from about 18°-25°C.) and was analyzed by thin-layer chromatography (TLC) using silica gel plates, developed with ether-hexane (1:1) and detected with ultraviolet light. Analysis revealed the desired imino chloride, $R_f=0.70$, and an absence of starting lactam.

Excess phosphorous oxychloride, was removed in vacuo using a rotary evaporator. The brown syrupy residue was dissolved in 1500 milliliters (ml) of toluene, treated with 500 ml of an ice-water mixture and stirred for 30 minutes. The toluene layer was separated, washed twice with 200 ml of water and dried with anhydrous magnesium sulfate. After removal of the drying agent by filtration, the filtrate was concentrated in vacuo using a rotary evaporator to give the crude imino chloride as a light yellow solid: 115.15 g (92.6% yield): m.p. 106°-108°.

(d) Dibenzo[b,f][1,4]thiazepine-11(10H)one.

Polyphosphoric acid (1.2 mole) was heated at 65° C. and phenyl 2-(phenylthio-phenylcarbamate (0.16 mole) added with stirring. The reaction was heated to 100° C.±5° C. and maintained at this temperature for 6 hours. The reaction was cooled to about 80° C. and water (1.5 liters) was added slowly. After cooling to ambient temperature the product was filtered off as an off-white solid, washed sparingly with acetone and dried. The yield was about 87%.

(e) Phenyl 2-(phenylthio)phenylcarbamate.

2-Amino diphenylsulfide (0.4 mole) was dissolved in toluene (500 ml) and cooled to 5° C. Phenyl chloroformate (0.24 mole) in toluene (50 ml) was added slowly to the stirred solution over 1 hour. When addition was complete a simultaneous addition of phenyl chloroformate (0.24 mole) in toluene (50 ml) and an aqueous solution of sodium hydroxide (0.3 mole) and sodium carbonate (0.35 mole) (200 ml) was started.

After completing the addition, the reaction was stirred for 1 hour. The aqueous phase was discarded and the organic phase was washed with dilute hydrochloric acid. The organic phase was dried over magnesium sulfate. After filtration the toluene was removed in vacuo. Recrystallization of the residue from hexane afforded the urethane in about 90% yield.

EXAMPLE A

Tablets
Each tablet contains:

| Compound of formula II | 5 mg |
|---|---|
| Lactose | 88 mg |
| Magnesium stearate | 1 mg |
| Polyvinylpyrrolidone | 2 mg |
| Sodium starch glycolate | 4 mg |

The compound of formula II, lactose, and a portion of the sodium starch glycolate and the polyvinylpyrrolidone are mixed in a suitable mixer and water added until the desired mass for granulation is obtained. The mass obtained may be passed through a suitable size mesh and dried to obtain the optimum moisture content. The remaining sodium starch glycolate and magnesium stearate is then added and the dry granulate is then passed through a further screen before final blending and compression to yield tablets each weighing 100 mg.

EXAMPLE B

Tablets:
Each tablet contains:

| Compound of formula II | 250 mg |
|---|---|
| Lactose | 122 mg |
| Magnesium stearate | 4 mg |
| Pregelatinized Starch | 8 mg |
| Sodium starch glycolate | 16 mg |

The tablets are formulated as described in Example A to yield tablets each weighing 600 mg. The pregelatinized starch replaces the polyvinylpyrrolidone.

EXAMPLE C

Tablets:
Each tablet contains:

| Compound of formula II | 100 mg |
|---|---|
| Lactose | 84 mg |
| Stearic Acid | 4 mg |
| Pregelatinized starch | 4 mg |
| Starch (maize) | 8 mg |

The tablets are formulated as described in Example A to yield tablets each weighing 200 mg. The stearic acid pregelatinized starch and starch (maize) replace the magnesium stearate, polyvinylpyrrolidone and sodium starch glycolate.

What is claimed is:

1. A compound of formula II

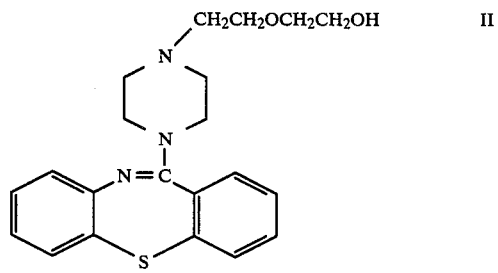

and acid addition salts thereof.

2. A compound as claimed in claim 1 wherein said acid addition salts are phamaceutically acceptable acid addition salts.

3. A compound as claimed in claim 2 wherein said salt is a hemifumarate salt.

4. A compound as claimed in claim 2 wherein said salt is a hydrochloride salt.

5. A pharmaceutical composition comprising a compound of claim 2 in an amount sufficient to manage a psychotic condition in a living mammal in need of such treatment in association with a non-toxic pharmaceutically acceptable diluent or carrier.

6. A pharmaceutical composition comprising a compound of claim 2 in an amount sufficient to reduce hyperactivity in a living mammal in need of such treatment in association with a non-toxic pharmaceutically acceptable diluent or carrier.

7. A method of treating psychosis in a living mammal comprising administering to the mammal an effective amount of a composition of claim 2.

8. A method of treating hyperactivity in a living mammal comprising administering to the mammal an effective amount of a composition of claim 2.

* * * * *

UNITED STATES PATENT AND TRADEMARK OFFICE
CERTIFICATE OF CORRECTION

PATENT NO. : 4,879,288

DATED : NOVEMBER 7, 1989

INVENTOR(S) : WARAWA, ET AL.

It is certified that error appears in the above-identified patent and that said Letters Patent is hereby corrected as shown below:

Column 1, line, 53 "facial-buc-cal-cervical" should read --facial-buccal-cervical--.

Column 3, line, 68 "dimethylforamide" should read --dimethylformamide--.

Column 6, line, 9 "formula XVII" should read --formula XVIII--.

Column 6, line, 10 "diphenysulfide" should read --diphenylsulfide--.

Column 6, line, 33 "1.0 ° 40" should read --1.0 to 40--.

Column 6, line, 51 "-1-piperaziny]" should read ---1-piperazinyl]--.

Column 7, line, 59 "-1-piperaziny]" should read ---1-piperazinyl]--.

Column 8, line, 6 "-1-piperaziny]" should read ---1-piperazinyl]--.

UNITED STATES PATENT AND TRADEMARK OFFICE
CERTIFICATE OF CORRECTION

PATENT NO. : 4,879,288
DATED : NOVEMBER 7, 1989
INVENTOR(S) : WARAWA, ET AL.

It is certified that error appears in the above-identified patent and that said Letters Patent is hereby corrected as shown below:

Column 8, line, 22 "-1-piperaziny]" should read ---1-piperazinyl]--.

Column 9, line, 9 "13 ° 14" should read --13 to 14--.

Column 9, line, 26 "Hyperactive" should read --Hyperactivity--.

Column 9, line, 32 "become hyperactivity." should read --become hyperactive.--.

Column 9, line, 48 "aaphetamine" should read --amphetamine--.

Column 10, line, 48 "stiulus" should read --stimulus--.

Column 12, line, 6 "(4 mmole)." should read --(14 mmole).--.

Signed and Sealed this

Twenty-fifth Day of January, 1994

Attest:

BRUCE LEHMAN

Attesting Officer

Commissioner of Patents and Trademarks